United States Patent
Kim et al.

(10) Patent No.: US 12,193,744 B1
(45) Date of Patent: Jan. 14, 2025

(54) LARGE VESSEL OCCLUSION TEST DEVICE AND METHOD USING EYEBALL DEVIATION

(71) Applicant: Heuron Co., Ltd., Seoul (KR)

(72) Inventors: Dohyun Kim, Suwon-si (KR); Soohwa Song, Incheon (KR)

(73) Assignee: Heuron Co., Ltd., Seoul (KR)

( * ) Notice: Subject to any disclaimer, the term of this patent is extended or adjusted under 35 U.S.C. 154(b) by 0 days.

(21) Appl. No.: 18/744,064

(22) Filed: Jun. 14, 2024

(30) Foreign Application Priority Data

Oct. 11, 2023 (KR) .......... 10-2023-0135051

(51) Int. Cl.
*A61B 3/113* (2006.01)
*G06T 7/00* (2017.01)

(52) U.S. Cl.
CPC .......... *A61B 3/113* (2013.01); *G06T 7/0012* (2013.01); *G06T 2207/10081* (2013.01); *G06T 2207/20084* (2013.01); *G06T 2207/30041* (2013.01)

(58) Field of Classification Search
CPC .......... A61B 3/113; G06T 7/0012; G06T 2207/10081; G06T 2207/20084; G06T 2207/30041
See application file for complete search history.

(56) References Cited

U.S. PATENT DOCUMENTS

2019/0192089 A1   6/2019   Maresky et al.

FOREIGN PATENT DOCUMENTS

| | | |
|---|---|---|
| JP | 2021-183113 A | 12/2021 |
| JP | 2022-531514 A | 7/2022 |
| JP | 2022-127566 A | 8/2022 |
| KR | 101540254 B1 | 7/2015 |
| KR | 101702267 B1 | 2/2017 |
| KR | 101860566 B1 | 5/2018 |
| KR | 102058884 B1 | 12/2019 |
| KR | 102068836 B1 | 2/2020 |
| KR | 102189623 B1 | 12/2020 |
| KR | 102410254 B1 | 6/2022 |

OTHER PUBLICATIONS

Korean Office Action dated Dec. 11, 2023 in Application No. 10-2023-0135051, 5 pages.
Korean Office Action dated Feb. 14, 2024 in Application No. 10-2023-0135051, 5 pages.

*Primary Examiner* — Michael T Rozanski
(74) *Attorney, Agent, or Firm* — Sughrue Mion, PLLC

(57) ABSTRACT

A large vessel occlusion (LVO) test device using eyeball deviation includes an image input unit configured to input non-contrast computed tomography (CT); a pre-processing unit; an image processing unit; and a determination unit. The objects include both eyes and the upper part of the brain corresponding to the entire cerebral cortex from the midbrain. The image processing unit configured to non-rigid register at least one atlas for the non-cis contrast CT images pre-processed from the pre-processing unit, normalize each cell of the non-contrast CT image to which the atlas is registered to have a value of 0 or 1, and extract a region of interest in a restored non-contrast CT image by combining each cell of the non-contrast CT image to which the atlas is registered through inverse transformation.

12 Claims, 6 Drawing Sheets

LARGE VESSEL OCCLUSION TEST DEVICE AND METHOD USING EYEBALL DEVIATION

CROSS-REFERENCE TO RELATED APPLICATIONS

This application claims the priority of Korean Patent Application No. 10-2023-0135051 filed on Oct. 11, 2023, in the Korean Intellectual Property Office, the disclosure of which is incorporated herein by reference.

BACKGROUND

Field

The present disclosure relates to acute large vessel occlusion test device and method using eyeball deviation, and more particularly, to acute large vessel occlusion test device and method using eyeball deviation capable of performing an acute large vessel occlusion (LVO) test using eyeball deviation, which is a biomarker identified from non-contrast computed tomography (NCCT) of a patient.

Description of the Related Art

Time is a representative factor that most influences the prognosis of patients with acute large vessel occlusion (hereinafter referred to as 'LVO'). Since 1998, in the case of acute ischemic stroke, there has been no method for treating large vessel occlusion (LVO) reperfusion other than an intravenous tissue plasminogen activator (tPA) within 4.5 hours after symptom onset. However, the treatment of LVO patients reached a turning point through the 'MR CLEAN' cohort study in 2015, but it was proven through several studies that reperfusion by mechanical thrombectomy improved the prognosis of LVO patients.

In addition, according to several study results, it was shown that endovascular treatment is possible for up to 16 or 24 hours in patients who meet several conditions, such as location of LVO, National Institutes of Health Stroke Scale (NIHSS), and lesion nucleus size.

However, in order to practically consider the prognosis of endovascular treatment, it is generally recommended to perform treatment within 6 hours, and in the case of LVO patients, receiving appropriate treatment through rapid diagnosis is known as a method for saving the patient's life and quickly returning to the daily life of patients.

In addition, many studies reached a result that patients do not still receive endovascular treatment within an appropriate time due to time delay caused by transfer to other hospitals to lower the likelihood of a good prognosis.

Meanwhile, when a patient visits the hospital due to symptoms suspected of LVO, it is common to first perform non-contrast CT scanning after analyzing the basic condition of the patient. Generally, the first symptom confirmed through non-contrast CT is the presence of cerebral hemorrhage, and when no evidence of cerebral hemorrhage is found, the patient is scanned based on CT Angiography (CTA), CT Perfusion (CTP), or magnetic resonance diffusion weighted image (MR DWI).

Such angiography (CTA), CT perfusion (CTP), or magnetic resonance diffusion weighted image (MR DWI) may not be performed depending on a clinical environment or a patient's condition, such as contrast agent allergy. In contrast, non-contrast computed tomography has few limitations to be considered and has an advantage of being able to scan patients relatively easily compared to other scanning methods.

However, compared to other scanning methods, the non-contrast computed tomography has a problem that it is difficult to clearly identify symptoms of LVO patients, and as a result, there is a large difference in symptom identification results depending on the subjective experience of radiologists. Such a non-objective symptom identification result is the reason why there is a problem in difference between interferers in the Alberta Stroke Program Early Computed Tomographic Score (ASPECTS) calculated based on non-contrast CT.

According to a previous study, it was confirmed that an average time of door-to-CT imaging required to scan the LVO patient by non-contrast computed tomography after visiting the hospital and an average time of door-to-CTA required to scan the LVO patient using angiography after visiting the hospital were 13.4±1.8 and 75.5±44.5 minutes, respectively.

In other words, when a medical staff may quickly analyze the condition of the LVO patient, it is expected that the test and treatment times for the LVO patient will be shortened in various clinical environments. In addition, when the LVO patient may be quickly identified through non-contrast computed tomography, which require less time to scan the patient, it is expected that early identification of the LVO patient will be possible not only in tertiary hospitals (general hospitals), but also in primary and secondary hospitals where only non-contrast computed tomography scanning is possible.

According to this need, a test is conducted to determine whether the patient is LVO positive or negative based on the non-contrast computed tomography, and there is a need for research and development of large vessel occlusion test device and method capable of inducing the treatment of the patient to be rapidly performed by providing the notification to the medical staff when the patient is determined to be LVO positive.

RELATED ART DOCUMENT

[Patent Document]
  Korean Patent Registration No. 10-1702267 (issued on Jan. 25, 2017)

SUMMARY

An object of the present disclosure is to provide large vessel occlusion test device and method using eyeball deviation capable of performing an LVO test using eyeball deviation which is a biomarker to be identified from non-contrast computed tomography of a patient.

In addition, another object of the present disclosure is to provide large vessel occlusion test device and method using eyeball deviation capable of inducing the treatment of a patient to be rapidly performed by providing a notification to a medical staff when the patient is determined to be LVO positive according to a result of the LVO test.

In addition, yet another object of the present disclosure is to provide large vessel occlusion test device and method using eyeball deviation capable of determining whether a patient is LVO positive or negative by a plurality of biomarkers to be identified from non-contrast computed tomography of a patient as well as eyeball deviation.

Specifically, yet another object of the present disclosure is to provide large vessel occlusion test device and method using eyeball deviation capable of identifying dense MCA sign (DMS), early ischemic changes (EIC), and eyeball deviation from non-contrast computed tomography of a patient and determining whether a patient is LVO positive or negative based on the plurality of identified biomarkers.

However, the technical objects to be achieved in the present disclosure are not limited to the aforementioned technical objects, and other technical objects, which are not mentioned above, will be apparently understood to a person having ordinary skill in the art from the following description.

A large vessel occlusion test device according to an exemplary embodiment of the present disclosure may include an image input unit configured to input non-contrast computed tomography which is a sequence image consisting of a plurality of consecutive non-contrast CT images including at least anatomical objects which are objects consisting of both eyes and the upper part of the brain corresponding to the entire cerebral cortex from the midbrain; a pre-processing unit configured to pre-process the non-contrast CT images based on rigid registration and affine registration; an image processing unit configured to non-rigid register at least one atlas for the non-contrast CT images pre-processed from the pre-processing unit, normalize each cell of the non-contrast CT image to which the atlas is registered to have a value of 0 or 1, and extract a region of interest in a restored non-contrast CT image by combining each cell of the non-contrast CT image to which the atlas is registered through inverse transformation; and a determination unit configured to identify eyeball deviation from the non-contrast CT image from which the region of interest is extracted, determine the patient to be LVO positive or negative by performing the LVO test based on the eyeball deviation, classify LVO suspected cases of the patient determined to be LVO positive through the LVO test, and then provide a notification to a medical staff.

A large vessel occlusion test method according to an exemplary embodiment of the present disclosure performed by the large vessel occlusion test device may include a first step of inputting, by an image input unit, non-contrast computed tomography which is a sequence image consisting of a plurality of consecutive non-contrast CT images including at least anatomical objects which are objects consisting of both eyes and the upper part of the brain corresponding to the entire cerebral cortex from the midbrain; a second step of pre-processing, by a pre-processing unit, the non-contrast CT images based on rigid registration and affine registration; a third step of non-rigid registering, by an image processing unit, at least one atlas for the non-contrast CT images pre-processed from the pre-processing unit, normalizing each cell of the non-contrast CT image to which the atlas is registered to have a value of 0 or 1, and extracting a region of interest in a restored non-contrast CT image by combining each cell of the non-contrast CT image to which the atlas is registered through inverse transformation; and a fourth step of identifying, by a determination unit, eyeball deviation from the non-contrast CT image from which the region of interest is extracted, determining the patient to be LVO positive or negative by performing the LVO test based on the eyeball deviation, classifying LVO suspected cases of the patient determined to be LVO positive through the LVO test, and then providing a notification to a medical staff.

According to the exemplary embodiment of the present disclosure, it is possible to induce the treatment of a patient to be rapidly performed by conducting an LVO test for determining whether the patient is LVO positive or negative based on non-contrast computed tomography and providing the notification to a medical staff when the patient is determined to be LVO positive.

According to the exemplary embodiment of the present disclosure, it is possible to improve a problem with limitations in determining whether a patient is LVO positive or negative through each biomarker, by using dense MCA sign (DMS), early ischemic changes (EIC), and eyeball deviation identified from non-contrast computed tomography of the patient.

However, effects which may be obtained in the present disclosure are not limited to the aforementioned effects and other unmentioned effects will be clearly understood by those skilled in the art from the following description.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Figure 1:
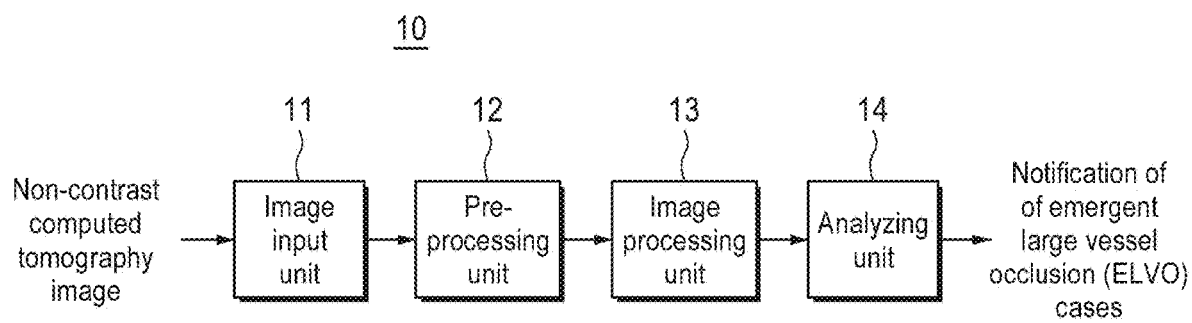
FIG. 1 is a block diagram of a large vessel occlusion test device according to an exemplary embodiment of the present disclosure.

Hereinafter, exemplary embodiments of the present disclosure will be described in detail so as to be easily implemented by those skilled in the art, with reference to the accompanying drawings. A description of the present disclosure is merely an exemplary embodiment for a structural or functional description and the scope of the present disclosure should not be construed as being limited by exemplary embodiments described in a text. That is, since the exemplary embodiment may be variously changed and have various forms, the scope of the present disclosure should be understood to include equivalents capable of realizing the technical spirit. Further, since a specific exemplary embodiment should not include all objects or effects or include only the effect, it should not be understood that the scope of the present disclosure is limited by the object or effect.

Meanings of terms described in the present disclosure should be understood as follows.

The terms "first", "second", and the like are used to differentiate a certain component from other components, but the scope should not be construed to be limited by the terms. For example, a first component may be referred to as a second component, and similarly, the second component may be referred to as the first component. It should be understood that, when it is described that a component is "connected to" the other component, the component may be directly connected to the other component or another component may be present therebetween. In contrast, it should be understood that when it is described that a component is "directly connected to" the other component, another component is not present therebetween. Meanwhile, other expressions describing the relationship between the components, that is, expressions such as "between" and "directly between" or "adjacent to" and "directly adjacent to" should be similarly interpreted.

It is to be understood that the singular expression encompass a plurality of expressions unless the context clearly dictates otherwise and it should be understood that term "including" or "having" indicates that a feature, a number, a step, an operation, a component, a part or the combination thereof described in the specification is present, but does not exclude a possibility of presence or addition of one or more other features, numbers, steps, operations, components, parts or combinations thereof, in advance.

If it is not contrarily defined, all terms used herein have the same meanings as those generally understood by those skilled in the art. Terms which are defined in a generally used dictionary should be interpreted to have the same meaning as the meaning in the context of the related art, and are not interpreted as an ideal meaning or excessively formal meanings unless clearly defined in the present disclosure.

Acute Large Vessel Occlusion Test Device

In the present disclosure, non-contrast computed tomography (NCCT) refers to a computed tomography image obtained without using a contrast agent solution, and more specifically, preferably a sequence image consisting of a plurality of consecutive non-contrast CT images that include at least anatomical objects which are objects forming both eyeballs (both eyes) and the upper part of the brain including the entire cerebral cortex and the like from the midbrain of a subject (patient) to be imaged.

In addition, the non-contrast computed tomography may be captured with a slice thickness of 5 mm or less from imaging equipment so that a determination unit 14 to be described below may extract a dense MCA sign (DMS).

The large vessel occlusion test device 10 of the present disclosure may be implemented with radiology computer-assisted classification and notification (CADt) software designed to enable image analysis of non-contrast computed tomography, in order to support workflow classification of the hospital network and its users, radiologists, by displaying the occlusion when the occlusion findings of the internal carotid artery (ICA) or middle cerebral artery (MCA) are suspected in the non-contrast computed tomography.

Hereinafter, the large vessel occlusion test device 10 according to an exemplary embodiment of the present disclosure, which may be implemented through software as described above, will be described in detail with reference to the accompanying drawings.

FIG. 1 is a block diagram of a large vessel occlusion test device according to an exemplary embodiment of the present disclosure.

Referring to FIG. 1, the large vessel occlusion test device 10 includes an image input unit 11, a pre-processing unit 12, an image processing unit 13, and a determination unit 14.

The image input unit 11 inputs non-contrast computed tomography consisting of a plurality of non-contrast CT images including at least both eyes and the upper part of the brain, including the entire cerebral cortex and the like from the midbrain of a subject to be imaged to determine whether the patient is LVO positive or negative from imaging equipment for capturing the non-contrast computed tomography.

The image input unit 11 is not limited to acquiring a plurality of non-contrast CT images from imaging equipment, and may input non-contrast computed tomography consisting of a plurality of non-contrast CT images by a data set input method.

The pre-processing unit 12 receives the non-contrast computed tomography from the image input unit 11 and pre-processes a plurality of non-contrast CT images constituting the received non-contrast computed tomography.

More specifically, the pre-processing unit 12 generates a first non-contrast CT image that is a reference non-contrast CT image (reference image) from the plurality of non-contrast CT images, and may extract each landmark point of second non-contrast CT images, which are other floating non-contrast CT images except for the first non-contrast CT image.

In the present disclosure, the landmark points of the first non-contrast CT image and the second non-contrast CT images are extracted from objects consisting of both eyes and the upper part of the brain, including the entire cerebral cortex and the like from the midbrain, which are anatomical objects in the non-contrast CT image, and preferably at least two or more.

In addition, the pre-processing unit 12 generates a pre-processed non-contrast CT image by registering the second non-contrast CT image to the first non-contrast CT image based on matching the landmark points extracted based on rigid registration and affine registration to complete the pre-processing of the first non-contrast CT image and the second non-contrast CT image and transmits the pre-processed non-contrast CT image to the image processing unit 13.

In the present disclosure, the rigid registration and affine registration refer to a process of global registration of the first non-contrast CT image and the second non-contrast CT image, and the anatomical object is treated and registered as a rigid body.

The image processing unit 13 performs processes of receiving the pre-processed non-contrast CT image from the pre-processing unit 12, synchronizing the pre-processed non-contrast CT image to a standard atlas template, and registering the pre-processed non-contrast CT image in a space of the standard atlas template.

At this time, the atlas template refers to a new tool of Voyager, which is cloud-based software for analyzing CT scan data.

In addition, the image processing unit 13 non-rigidly registers at least one atlas to the pre-processed non-contrast CT image registered in the space of the standard atlas template, so that the atlas is as similar as possible to the pre-processed non-contrast CT image.

In the present disclosure, the atlas may be an image pair of objects consisting of both eyes and the upper part of the brain, including the entire cerebral cortex and the like from the midbrain, which are anatomical objects, and may be used to segment the pre-processed non-contrast CT image into anatomical objects.

In the present disclosure, the image processing unit 13 may non-rigidly register the atlas based on multi-scaled and phase-based registration.

In addition, the atlas may be modified to correspond to the shape with the pre-processed non-contrast CT image by non-rigid registration performed from the image processing unit 13 and registered into a group of anatomical objects.

In addition, the image processing unit 13 adds the registration result of the atlas to the pre-processed non-contrast CT image, and forms the atlas-registered non-contrast CT image on the standard atlas template.

In the present disclosure, the atlas-registered non-contrast CT image may be a probability map that defines the probability that each cell constituting the pre-processed non-contrast CT image represents a volume of the anatomical object.

In addition, the image processing unit 13 normalizes the atlas-registered non-contrast CT image, and each cell of the atlas-registered non-contrast CT image has a value of 0 or 1 through normalization.

At this time, a value of 1 is given when the volume of the anatomical object is included in part or the entire area of the cell, and a value of 0 is given when the volume of the anatomical object is not included in the entire area of the cell.

In the present disclosure, the atlas-registered non-contrast CT image is segmented into not only the vascular regions of the internal carotid artery (ICA) and middle cerebral artery (MCA), but also the cortical and subcortical areas affected by the ICA and the MCA through normalization performed from the image processing unit 13.

In addition, the image processing unit 13 combines each cell of the non-contrast CT image to which the atlas with a value of 0 or 1 is registered, through a normalization process through inverse transformation, so that the non-contrast CT image is restored, and as a result, extracts a region of interest (ROI) from the restored non-contrast CT image.

In the present disclosure, the ROI refers to a set of cells of the atlas-registered non-contrast CT image, to which the image processing unit 13 gives a value of 1 through the normalization process.

In addition, the image processing unit 13 transmits a non-contrast CT image from which the ROI is extracted to the determination unit 14.

The determination unit 14 receives a non-contrast CT image from which the ROI is extracted from the image processing unit 13, performs an LVO test for determining whether the patient is LVO positive or negative based on analyzing the received non-contrast CT image from which the ROI is extracted, and performs the learning using an artificial intelligence model (AI Model) to classify LVO suspected cases of a patient determined to be LVO positive through the LVO test.

Figure 2:
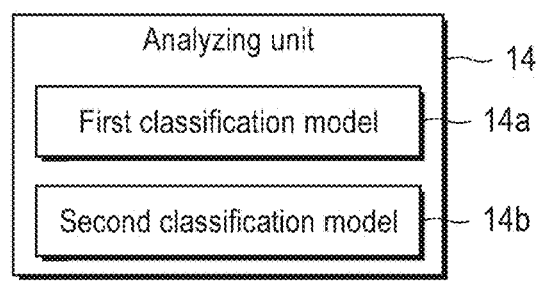
FIG. 2 is a block diagram of a classification model used for model learning to implement a determination unit illustrated in FIG. 1.

In the present disclosure, the determination unit 14 may perform learning using an AI model using classification models 14a and 14b illustrated in FIG. 2.

FIG. 2 is a block diagram of a classification model used for model learning to implement the determination unit illustrated in FIG. 1.

Referring to FIG. 2, the classification model for model learning of the determination unit 14 includes a first classification model 14a and a second classification model 14b.

The first classification model 14a is an AI model for learning a model so that the determination unit 14 performs an LVO test to determine a patient as LVO positive or negative based on analyzing the non-contrast CT image from which the ROI is extracted.

As a specific example, the first classification model 14a may be implemented using 2D and 3D convolutional neural networks (CNN), and the 2D CNN may be EfficientNet.

Since the EfficientNet is an AI model that typically belongs to a convolutional neural network, a detailed description thereof will be omitted for convenience.

The second classification model 14b is an AI model for learning the model so that the determination unit 14 classifies LVO suspected cases of a patient determined to be LVO positive.

As a specific example, the second classification model 14b may be implemented using a recurrent neural network (RNN)-based bidirectional LSTM (Bi-LSTM) model.

Since the Bi-LSTM model is an AI model that typically belongs to an RNN, a detailed description thereof will be omitted for convenience.

Meanwhile, the first classification model 14a is an AI model for learning a model so that the determination unit 14 performs an LVO test to determine whether the patient is LVO positive or negative based on identifying the features of a biomarker, which is a symptom indicator of LVO positive, from the non-contrast CT image from which the ROI is extracted.

In the present disclosure, the biomarker includes dense MCA sign (DMS), early ischemic changes (EIC), and eyeball deviation, which are symptomatic indicators of LVO positive.

Here, the dense MCA sign (DMS) is a phenomenon in which the artery is blocked by the thrombus, and also a phenomenon in which cerebral arteries in the blocked area appear excessively in non-contrast computed tomography image. The dense MCA sign (DMS) is a representative biomarker describing occlusion of the middle cerebral artery (MCA) in non-contrast computed tomography image but has a limitation that its presence or absence is determined depending on a slice thickness setting of the scanned non-contrast computed tomography image. Typically, the dense MCA sign (DMS) is characterized by a higher probability of detection as the slice thickness of the non-contrast computed tomography becomes thinner.

In addition, the early ischemic changes (EIC) are a term that refers to ischemic changes that occur in brain tissue after large vessel occlusion (LVO), and identified from the non-contrast computed tomography captured early after the large vessel occlusion. At this time, if the middle cerebral artery (MCA) is blocked by the thrombus, the early ischemic changes (EIC) may be identified in the lower brain, such as in the catalytic infection or basal ganglia after occurrence of the stroke. According to a phenomenon of early ischemic changes (EIC), the Alberta Stroke Program Early CT Scores M1-M6 (ASPECTS M1-M6) were developed as a representative scoring system that inspected areas where lesions occurred in areas such as the middle cerebral artery (MCA) and basal ganglia.

In addition, for eyeball deviation, the acute ischemic stroke is known as a single-sided disease, and symptoms of ischemic changes appear in the opposite hemisphere where LVO occurred, and these ischemic changes may be confirmed by gaze paralysis, but in LVO patients, the eyes are biased toward the hemisphere where LVO occurred. In particular, a result of a study that classified LVO patients based on the eye deviation observed in CT images has been recently reported, and as a result of using the eye deviation as a single index for classifying LVO patients, it was confirmed that the sensitivity was 71% and the specificity was 77.5%.

The biomarker of the present disclosure is a representative indicator used to determine whether a patient is LVO positive or negative, but when used independently, there are limitations in determining whether the patient is LVO positive or negative.

In the present disclosure, in order to determine whether the patient is LVO positive or negative by improving the limitations of each biomarker, the determination unit 14 preferably learns the model so that dense MCA sign (DMS), early ischemic changes (EIC), and eyeball deviation as biomarkers are identified from the non-contrast CT image from which the ROI is extracted through the first classification model 14a.

In addition, when the patient is determined to be LVO positive through the LVO test, the determination unit 14 provides a notification to the medical staff that will treat the patient to induce rapid treatment of the patient.

In the present disclosure, the notification provided by the determination unit 14 to the medical staff may be provided to the medical staff through a server or application program accessible through a terminal (e.g., smartphone, PC, tablet, etc.).

In addition, the notification provided by the determination unit 14 to the medical staff includes LVO suspected cases of a patient determined to be LVO positive through the LVO test and compressed non-contrast CT images of the patient with a preview so that the medical staff refers to patient's conditions during the treatment.

Figure 3:
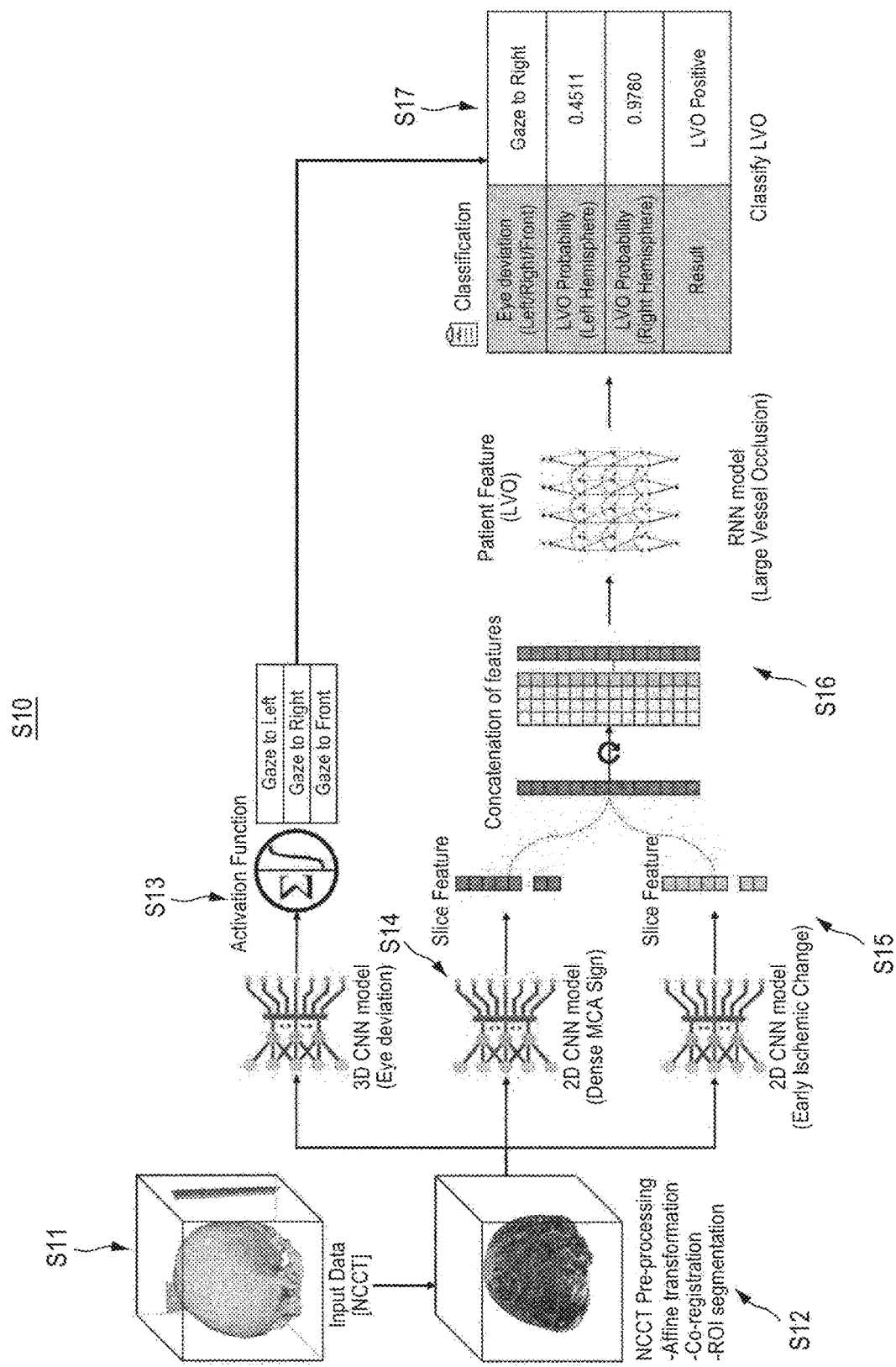
FIG. 3 is a flowchart of a large vessel occlusion test method according to an exemplary embodiment of the present disclosure.

In addition, as illustrated in FIG. 3, the LVO suspected cases of a patient may be generated and provided to medical staff in the form of data including eyeball deviation, LVO probability values for each of left and right hemispheres, and LVO determination results.

Acute Large Vessel Occlusion Test Method

Hereinafter, processes of a large vessel occlusion test method (S10) according to an exemplary embodiment of the present disclosure performed by the large vessel occlusion test device 10 will be described in detail.

Further, the large vessel occlusion test device 10 is preferably learned and trained to automatically perform the large vessel occlusion test method (S10) to be described below, and accordingly, the learning and training processes of the large vessel occlusion test method (S10) to be described below and the large vessel occlusion test device 10 may be the same as each other.

FIG. 3 is a flowchart of a large vessel occlusion test method according to an exemplary embodiment of the present disclosure.

Referring to FIG. 3, the large vessel occlusion test method (S10) includes an image input step (S11), an image processing step (S12), biomarker extraction steps (S13 to S15), an LVO probability value calculation step (S16) and an LVO testing and suspected case provision step (S17).

In the image input step (S11), the image input unit 11 may input non-contrast computed tomography captured with a slide thickness of 5 mm or less through imaging equipment or a data set input method.

In the image processing step (S12), the pre-processing unit 12 may pre-process a plurality of non-contrast CT images constituting the non-contrast computed tomography received from the image input unit 11.

At this time, the pre-processing unit 12 may pre-process (primary register) the non-contrast CT images based on rigid registration and affine registration in the image processing step (S12).

Further, in the image processing step (S12), the image processing unit 13 non-rigidly registers at least one atlas for the non-contrast CT image pre-processed in the space of the standard atlas template based on multi-scaled and phase-based registration so that the atlas is as similar as possible to the pre-processed non-contrast CT image.

In addition, the image processing unit 13 may normalize the non-contrast CT image to which the atlas is registered so that each cell of the non-contrast CT image to which the atlas is registered has a value of 0 or 1 in the image processing step (S12).

In addition, the image processing unit 13 combines each cell of the non-contrast CT image to which the atlas with a value of 0 or 1 is registered, through a normalization process through inverse transformation, in the image processing step (S12), so that the non-contrast CT image is restored, and as a result, may extract a region of interest (ROI) from the restored non-contrast CT image.

In the biomarker identification steps (S13 to S15), the determination unit 14 may identify each biomarker based on a convolutional neural network (CNN) when performing the LVO test.

The biomarker identification steps (S13 to S15) may include a first biomarker identification step (S13), a second biomarker identification step (S14), and a third biomarker identification step (S15).

In the first biomarker identification step (S13), the determination unit 14 may segment both eyes (eyeballs) from the non-contrast CT image from which the region of interest is extracted using a pre-trained 3D CNN model, and classify the segmented eyeball deviation into one of three classes of the front, left, and right sides.

At this time, in the first biomarker identification step (S13), the determination unit 14 may calculate probability values of the three classes (front, left, and right) for each of the left and right eyes as a value between 0 and 1, and classify eyeball deviation based on identifying a direction of the class with the highest probability value among the three classes into left and right eye directions.

In the second biomarker identification step (S14), the determination unit 14 tests an area from the end of the internal carotid artery (ICA) to an M1 segment of the middle cerebral artery (MCA) using a pre-trained first 2D CNN model to identify a dense MCA sign (DMS).

At this time, the determination unit 14 preferably identifies the dense MCA sign (DMS) of the left and right hemispheres, respectively, in the second biomarker identification step (S14).

In the third biomarker identification step (S15), the determination unit 14 tests an area to be expected when occlusion occurs from the end of the internal carotid artery (ICA) to an M2 segment of the middle cerebral artery (MCA) using the pre-trained first 2D CNN model to identify early ischemic changes (EIC).

At this time, the determination unit 14 preferably identifies early ischemic changes (EIC) in the left and right hemispheres, respectively, in the third biomarker identification step (S15).

In the LVO probability value calculation step (S16), the determination unit 14 may concatenate the features of a first 2D CNN model and a second 2D CNN model, and input the concatenated features into the RNN model to determine the LVO determination result of each of left and right hemispheres to be positive or positive.

In addition, the determination unit 14 may calculate the probability value of LVO of each of left and right hemispheres as a value between 0 and 1 based on the LVO determination result of each of left and right hemispheres in the LVO probability value calculation step (S16).

In the LVO testing and suspected case provision step (S17), the determination unit 14 may perform a test for determining whether LVO is positive or negative by extracting the features of the biomarkers identified from the biomarker extraction steps (S13 to S15) and the LVO probability value calculation step (S16), generate LVO suspected cases for a patient determined to be LVO positive through the test and then provide the generated LVO suspected cases to the medical staff.

At this time, the LVO suspected cases are generated in the form of data including eyeball deviation, LVO probability values for each of left and right hemispheres, and LVO discrimination results, and the LVO discrimination results may be calculated differently depending on the eyeball deviation and the LVO probability value of each of left and right hemispheres in the LVO test and suspected case provision step (S17).

FIGS. 4A to 6 are flowcharts illustrating detailed processes of a patient LVO data generation step illustrated in FIG. 3.

Figure 4A:
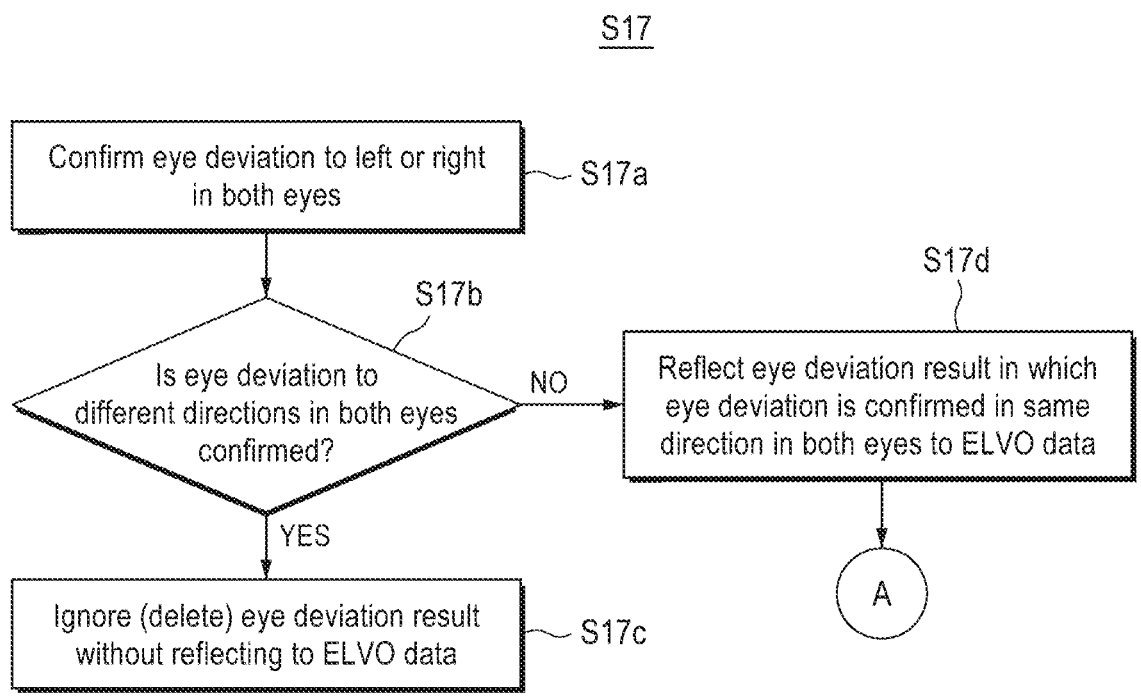
FIGS. 4A to 6 are flowcharts illustrating detailed processes of a patient LVO data generation step illustrated in FIG. 3.

Referring to FIG. 4A, when eye deviation to the left or right is confirmed in both eyes (S17a), the determination unit 14 may analyze whether eye deviation in different directions except for the front is confirmed in both eyes (S17b).

In Step (S17b), eye deviation in different directions means that both eyes face the left or right direction, excluding the front, such as the left eye facing left and the right eye facing right.

At this time, if deviation in different directions is confirmed in both eyes (S17b-YES), the determination unit 14 prevents the eyeball deviation extracted through the LVO test from being reflected in the data of the LVO suspected case (S17c).

Unlike this, if the deviation in the same direction is confirmed in both eyes (S17b—NO), the determination unit 14 allows the eyeball deviation extracted through the LVO test to be reflected in the data of the LVO suspected case (S17d).

Figure 4B:
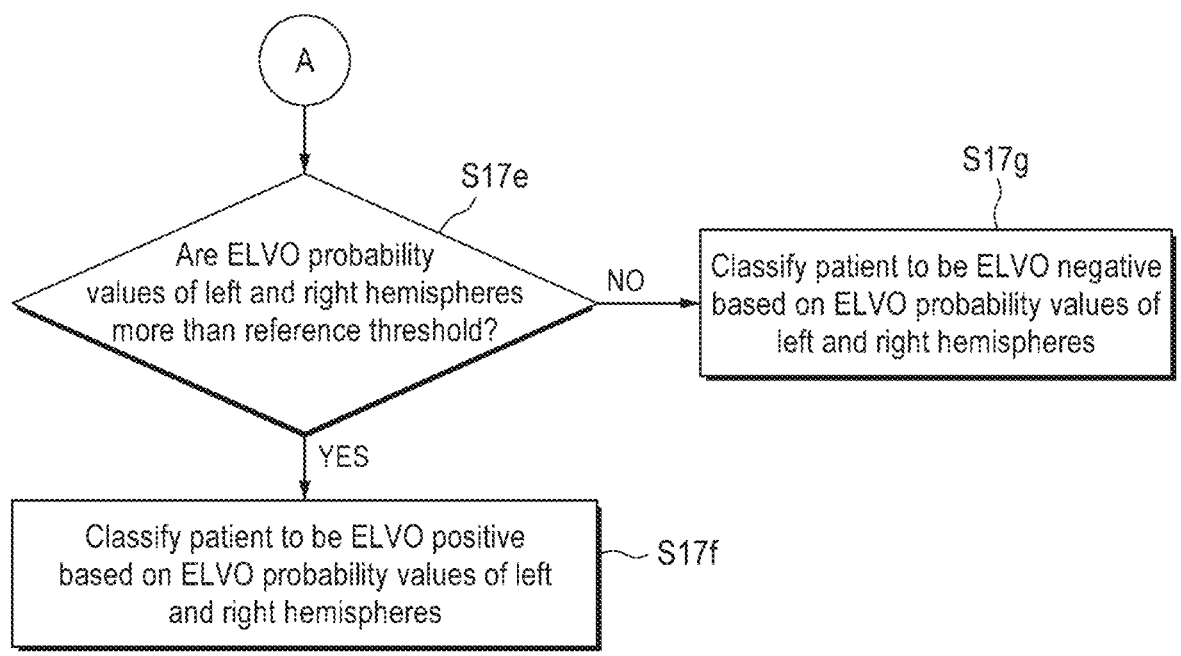

Referring to FIG. 4B, the determination unit 14 may determine whether the LVO probability value of each of left and right hemispheres exceeds a reference threshold in Step (S17d) (S17e).

At this time, if the LVO probability value of each of left and right hemispheres exceeds a reference threshold (S17e—YES), the determination unit 14 determines the patient to be LVO positive based on the LVO probability value of each of left and right hemispheres (S17f), so that the LVO positive determination results are reflected to the data of LVO suspected cases.

Unlike this, if the LVO probability value of each of left and right hemispheres is a reference threshold or less (S17e—NO), the determination unit 14 determines the patient to be LVO negative based on the LVO probability value of each of left and right hemispheres (S17g), so that the LVO negative determination results are reflected to the data of LVO suspected cases.

Figure 5:
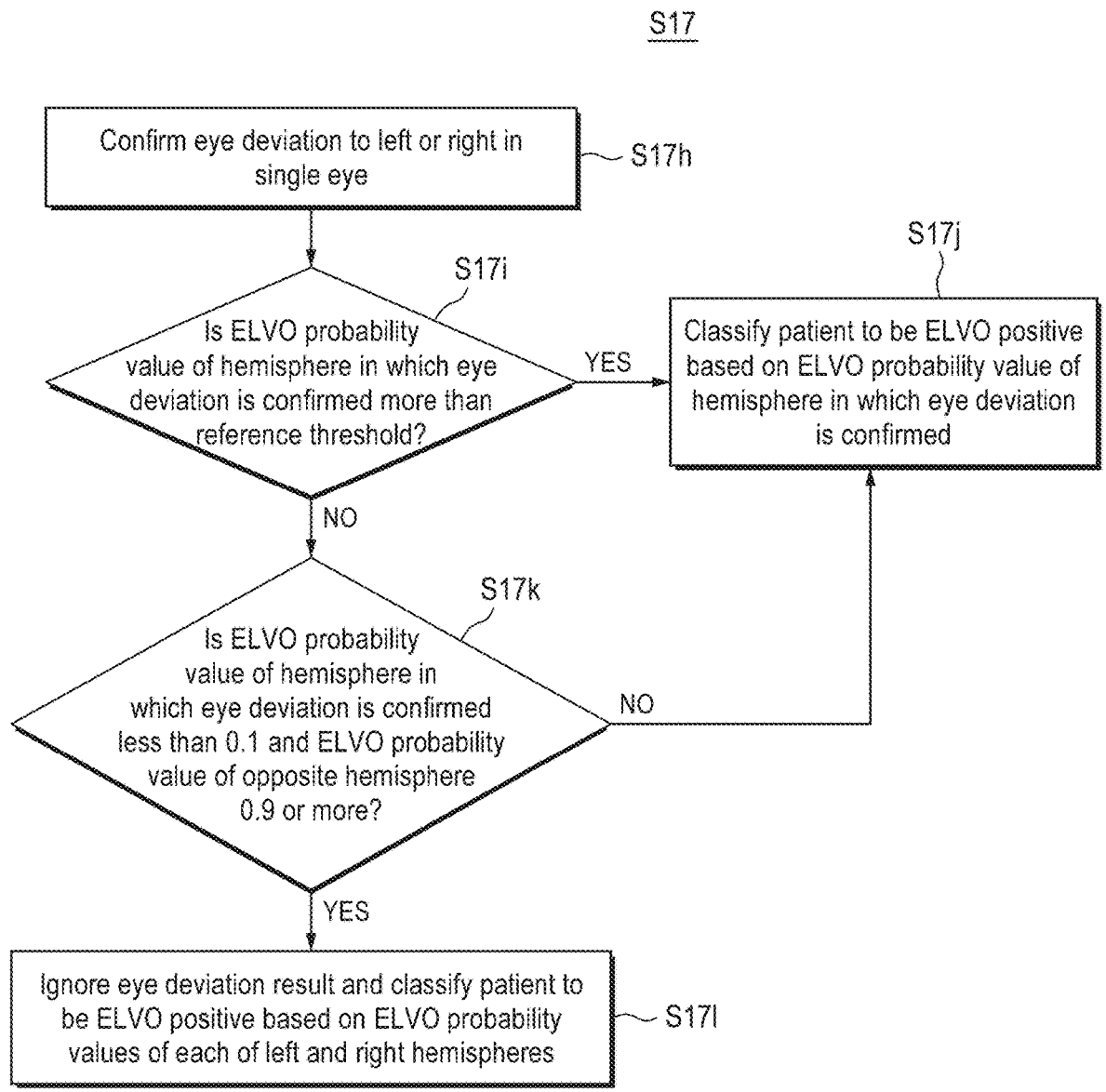

Referring to FIG. 5, when the deviation to the left or right excluding the front is confirmed only in the left or right eye (S17h), the determination unit 14 may determine whether the LVO probability value of the hemisphere in which eye deviation was confirmed exceeds the reference threshold (S17i). At this time, t the hemisphere in which the eye deviation is confirmed refers to a left or right hemisphere corresponding to the direction in which the left or right eye is facing.

At this time, if the LVO probability value of the hemisphere in which the eye deviation is confirmed exceeds a reference threshold (S17i—YES), the determination unit 14 determines the patient to be LVO positive based on the LVO probability value of the hemisphere in which the eye deviation is confirmed (S17j), so that the LVO positive determination results are reflected to the data of LVO suspected cases.

Unlike this, if the LVO probability value of the hemisphere in which the eye deviation is confirmed is a reference threshold or less (S17i—NO), the determination unit 14 may determine whether the LVO probability value of the hemisphere in which the eye deviation is confirmed is less than 0.1 and the LVO probability value of an opposite hemisphere is 0.9 or more (S17k).

At this time, if the LVO probability value of the hemisphere in which the eye deviation is confirmed is not less than 0.1 or the LVO probability value of the opposite hemisphere is not 0.9 or more (S17k—NO), the determination unit 14 determines the patient to be LVO positive based on the LVO probability value of the hemisphere in which the eye deviation is confirmed (S17j), so that the LVO positive determination results are reflected to the data of LVO suspected cases.

Unlike this, if the LVO probability value of the hemisphere in which the eye deviation is confirmed is less than 0.1 and the LVO probability value of the opposite hemisphere is 0.9 or more (S17k—YES), the determination unit 14 ignores the eye deviation results extracted through the LVO test and determines the patient to be LVO positive based on the LVO probability value of each of left and right hemispheres (S17l), so that the LVO positive determination results are reflected to the data of LVO suspected cases.

Figure 6:
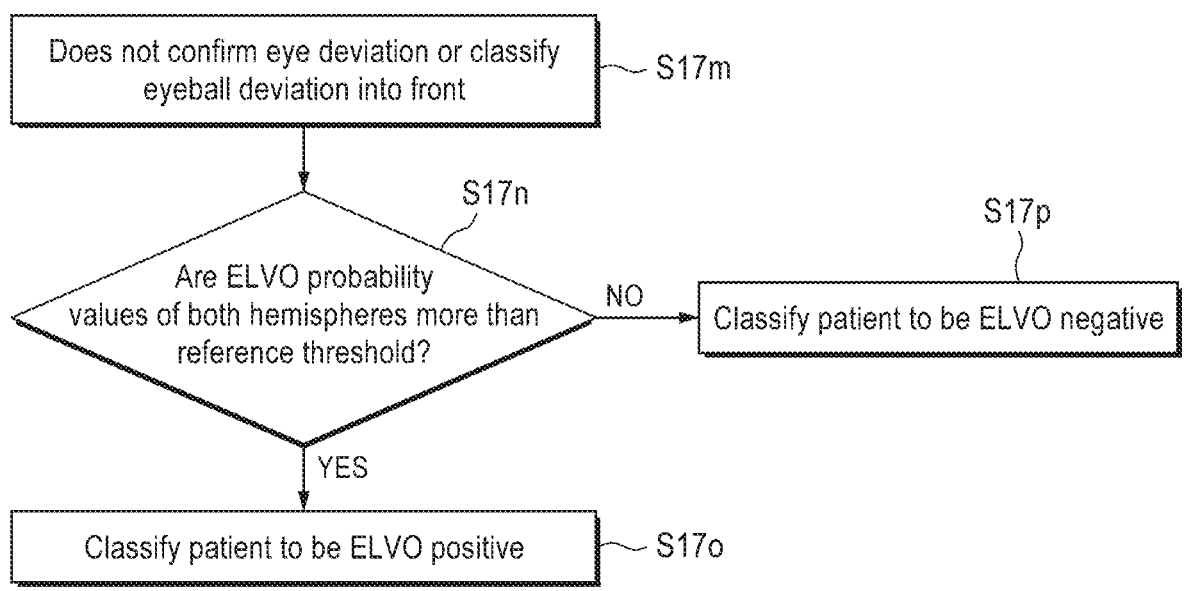

Referring to FIG. 6, when the deviation of at least one of the left and right eyes is not confirmed through the LVO test, or when the eyeball deviation is classified into the front (S17m), the determination unit 14 may determine whether the LVO probability value of each of left and right hemispheres exceeds a reference threshold (S17n).

At this time, if the LVO probability value of each of left and right hemispheres exceeds the reference threshold (S17n—YES), the determination unit 14 classifies the patient to be LVO positive (S17o), so that the positive LVO determination results are reflected to the data of LVO suspected cases.

Unlike this, if the LVO probability value of each of left and right hemispheres is the reference threshold or less (S17n—NO), the determination unit 14 classifies the patient to be LVO negative (S17p), so that the negative LVO determination results are reflected to the data of LVO suspected cases.

As described above, the detailed description of the exemplary embodiments of the disclosed present disclosure is provided such that those skilled in the art implement and carry out the present disclosure. While the present disclosure has been described with reference to the preferred exemplary embodiments, it will be understood by those skilled in the art that various changes and modifications of the present disclosure may be made without departing from the spirit and scope of the present disclosure. For example, those skilled in the art may use configurations disclosed in the above-described exemplary embodiments by combining them with each other. Therefore, the present disclosure is not intended to be limited to the above-described exemplary embodiments but to assign the widest scope consistent with disclosed principles and novel features.

The present disclosure may be embodied in other specific forms without departing from the spirit and essential features of the present disclosure. Therefore, the detailed description should not restrictively be analyzed in all aspects and should be exemplarily considered. The scope of the present disclosure should be determined by rational interpretation of the appended claims and all changes are included in the scope of the present disclosure within the equivalent scope of the present disclosure. The present disclosure is not intended to be limited to the above-described exemplary embodiments but to assign the widest scope consistent with disclosed principles and novel features. Further, claims having no clear quoting relation in the claims are combined to configure the exemplary embodiment or may be included as new claims by correction after application.

EXPLANATION OF REFERENCE NUMERALS AND SYMBOLS

10: Large vessel occlusion test device
11: Image input unit
12: Pre-processing unit
13: Image processing unit
14: Determination unit
14a: First classification model
14b: Second classification model

What is claimed is:

1. A large vessel occlusion test device using eyeball deviation comprising:
   an image input unit configured to input non-contrast computed tomography which is a sequence image consisting of a plurality of consecutive non-contrast computed tomography (CT) images including at least anatomical objects which are objects consisting of both eyes and the upper part of the brain corresponding to the entire cerebral cortex from the midbrain;
   a pre-processing unit configured to pre-process the non-contrast CT images based on rigid registration and affine registration;
   an image processing unit configured to non-rigid register at least one atlas for the non-contrast CT images pre-processed from the pre-processing unit, normalize each cell of the non-contrast CT image to which the atlas is registered to have a value of 0 or 1, and extract a region of interest in a restored non-contrast CT image by combining each cell of the non-contrast CT image to which the atlas is registered through inverse transformation; and
   a determination unit configured to identify eyeball deviation from the non-contrast CT image from which the region of interest is extracted, determine a patient to be large vessel occlusion (LVO) positive or negative by performing the LVO test based on the eyeball deviation, classify LVO suspected cases of the patient determined to be LVO positive through the LVO test, and then provide a notification to a medical staff.

2. The large vessel occlusion test device using eyeball deviation of claim 1, wherein the determination unit performs model learning to perform the LVO test and classify the LVO suspected cases.

3. The large vessel occlusion test device using eyeball deviation of claim 2, wherein the determination unit performs model learning through a first classification model which is 2D and 3D convolutional neural networks and a second classification model which is a recurrent neural network-based bidirectional long short-term memory (LSTM) model.

4. The large vessel occlusion test device using eyeball deviation of claim 3, wherein the first classification model is an artificial intelligence model for identifying the features of a biomarker, which is a symptom indicator of LVO positive, from the non-contrast CT image from which the region of interest is extracted.

5. The large vessel occlusion test device using eyeball deviation of claim 4, wherein the biomarker includes dense middle cerebral artery (MCA) sign (DMS), early ischemic changes (EIC), and eyeball deviation.

6. The large vessel occlusion test device using eyeball deviation of claim 5, wherein the determination unit performs the LVO test based on identifying the biomarker from the non-contrast CT image from which the region of interest is extracted.

7. The large vessel occlusion test device using eyeball deviation of claim 5, wherein the determination unit classifies the eyeball deviation into one of three classes of the front, left, and right sides, in the LVO test,
   determines an LVO determination result of each of left and right hemispheres to be positive or negative based on the dense MCA sign (DMS) and early ischemic changes (EIC), in the LVO test, and
   calculates an LVO probability value of each of left and right hemispheres as a value between 0 and 1 based on the LVO determination result of each of left and right hemispheres, in the LVO test.

8. The large vessel occlusion test device using eyeball deviation of claim 7, wherein the LVO suspected cases are data including the eyeball deviation, the LVO probability value of each of left and right hemispheres, and the LVO determination result of each of left and right hemispheres.

9. The large vessel occlusion test device using eyeball deviation of claim 8, wherein the notification includes LVO suspected cases of the patient and compressed non-contrast CT images of the patient with a preview.

10. The large vessel occlusion test device using eyeball deviation of claim 1, wherein the image processing unit gives a value of 1 when the volume of the anatomical object is included in part or the entire area of each cell of the non-contrast CT image to which the atlas is registered and a value of 0 when the volume of the anatomical object is not included in the entire area of the cell.

11. The large vessel occlusion test device using eyeball deviation of claim 1, wherein the atlas is an image pair of the anatomical object to segment the pre-processed non-contrast CT image into the anatomical object.

12. A large vessel occlusion test method using eyeball deviation comprising:
   a) a first step of inputting, by an image input unit, non-contrast computed tomography which is a sequence image consisting of a plurality of consecutive non-contrast computed tomography (CT) images including at least anatomical objects which are objects consisting of both eyes and the upper part of the brain corresponding to the entire cerebral cortex from the midbrain;
   b) a second step of pre-processing, by a pre-processing unit, the non-contrast CT images based on rigid registration and affine registration;
   c) a third step of non-rigid registering, by an image processing unit, at least one atlas for the non-contrast CT images pre-processed from the pre-processing unit, normalizing each cell of the non-contrast CT image to which the atlas is registered to have a value of 0 or 1, and extracting a region of interest in a restored non-contrast CT image by combining each cell of the non-contrast CT image to which the atlas is registered through inverse transformation; and
   d) a fourth step of identifying, by a determination unit, eyeball deviation from the non-contrast CT image from which the region of interest is extracted, determining a patient to be large vessel occlusion (LVO) positive or negative by performing the LVO test based on the eyeball deviation, classifying LVO suspected cases of the patient determined to be LVO positive through the LVO test, and then providing a notification to a medical staff.

* * * * *